United States Patent [19]

Baader et al.

[11] Patent Number: 5,130,317
[45] Date of Patent: Jul. 14, 1992

[54] PYRIMIDINE-4,6-DICARBOXYLIC ACID DIAMIDES, PROCESSES FOR THE USE THEREOF, AND PHARMACEUTICALS BASED ON THESE COMPOUNDS

[75] Inventors: Ekkehard Baader, Königstein/Taunus; Martin Bickel, Bad Homburg; Volkmar Günzler-Pukall, Marburg; Stephan Henke, Hofheim am Taunus, all of Fed. Rep. of Germany

[73] Assignee: Hoechst Aktiengesellschaft, Frankfurt am Main, Fed. Rep. of Germany

[21] Appl. No.: 584,655

[22] Filed: Sep. 19, 1990

[30] Foreign Application Priority Data

Sep. 21, 1989 [DE] Fed. Rep. of Germany ....... 3931432

[51] Int. Cl.$^5$ .................... A61K 31/53; A61K 31/505; A61K 31/50; A61K 31/495
[52] U.S. Cl. .................................... 514/256; 514/211; 514/212; 514/218; 514/227.8; 514/232.2; 514/235.8; 514/236.2; 514/236.5; 514/245; 514/252; 514/269; 514/272; 514/270; 514/271; 514/274; 514/275; 540/544; 540/575; 540/601; 544/122; 544/123; 544/120; 544/121; 544/114; 544/113; 544/82; 544/83

[58] Field of Search ............... 544/335, 333, 334, 310, 544/327, 316, 321, 238, 296, 113, 122, 121; 540/544; 514/256, 218, 235.8, 245, 272, 274

[56] References Cited

U.S. PATENT DOCUMENTS 5,010,200 4/1991 McDonald et al. ................ 544/335

Primary Examiner—John M. Ford
Attorney, Agent, or Firm—Finnegan, Henderson, Farabow, Garrett and Dunner

[57] ABSTRACT

Pyrimidine-4,6-dicarboxylic acid diamides, processes for the use thereof, and pharmaceuticals based on these compounds The invention relates to pyrimidine-4,6-dicarboxylic acid diamides of the formula I

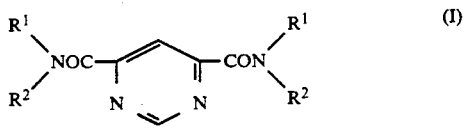

in which $R^1$ and $R^2$ have the meanings given. The compounds according to the invention inhibit proline hydroxylase and lysine hydroxylase and can be employed as fibrosuppressants and immunosuppressants.

8 Claims, No Drawings

PYRIMIDINE-4,6-DICARBOXYLIC ACID DIAMIDES, PROCESSES FOR THE USE THEREOF, AND PHARMACEUTICALS BASED ON THESE COMPOUNDS

Description

Compounds which inhibit the enzymes proline hydroxylase and lysine hydroxylase effect very selective inhibition of collagen biosynthesis by influencing collagen-specific hydroxlation reactions. In the course of these, protein-bonded proline or lysine is hydroxylated by the enzymes proline hydroxylase and lysine hydroxylase. If this reaction is suppressed by inhibitors, a hypo-hydroxylated collagen molecule which is not capable of functioning and can be released by the cells into the extracellular space in only a small amount is formed. The hypo-hydroxylated collagen also cannot be incorporated into the collagen matrix and is very readily degraded proteolytically. As a consequence of these effects, the total amount of extracellularly deposited collagen is reduced.

It is known that inhibition of proline hydroxylase by known inhibitors, such as $\alpha,\alpha'$-dipyridyl, leads to an inhibition of the $C1_q$ biosynthesis of macrophages (W. Müller et al., FEBS Lett. 90 (1978), 218; and Immunbiology 155 (1978), 47). This results in a loss of the classical route of complement activation. Inhibitors of proline hydroxylase therefore also act as immunosuppressants, for example in immunity complex diseases.

It is known that the enzyme proline hydroxylase is inhibited effectively by pyridine-2,4- or -2,5-dicarboxlic acid (K. Majamaa et al., Eur. J. Biochem. 138 (1984), 239-245). However, these compounds are effective as inhibitors in cell culture only in very high concentrations (Tschank, G. et al., Biochem. J. 238 (1987) 625-633).

DE-A 3,432,094 describes pyridine-2,4- and -2,5-dicarboxylic acid diesters having 1–6 carbon atoms in the ester alkyl part as pharmaceuticals for inhibiting proline hydroxylase and lysine hydroxylase.

However, these lower alkyl diesters have the disadvantage that they are split too rapidly in the organism to give the acids and do not arrive at their site of action in the cell in a sufficiently high concentration, and therefore are not particularly suitable for possible administration as pharmaceuticals.

DE-A 3,703,959, DE-A 3,703,962 and DE-A 3,703,963 describe, in the general form, mixed ester/amides, higher alkylated diesters and diamides of pyridine-2,4- and -2,5-dicarboxylic acid which effectively inhibit collagen biosynthesis in the animal model.

The synthesis of N,N,-bis(2-methoxy-ethyl)-pyridine-2,4-dicarboxylic acid diamide and N,N,-bis(3-isopropoxy-propyl)-pyridine-2,4-dicarboxylic acid diamide is thus described, inter alia, in DE-A 3,703,959.

An improved process for the preparation of N,N,-bis(2-methoxyethyl)-pyridine-2,4-dicarboxylic acid diamide is proposed in German Patent Applications P 38 26 471.4 and P 38 28 140.6. German Patent Application P 3924093.2 proposes novel N,N,-bis(alkoxyalkyl)-pyridine-2,4-dicarboxylic acid diamides.

Surprisingly, it has now been found that pyrinidine-4,6-dicarboxylic acid diamides of the formula I

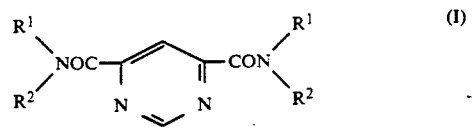

in which
R$^1$ is C$_1$–C-alkyl, C$_2$–C$_{12}$alkenyl or C$_2$–C$_{12}$-alkynyl, which are unsubstituted or monosubstituted or, in the case of C$_2$–C$_{12}$-alkyls, C$_2$–C$_{12}$-alkenyls and C$_2$–C$_{12}$-alkynyls, also polysubstituted by halogen, hydroxyl, cyano, amino, carboxyl, alkoxy, alkoxycarbonyl, alkylcarbonyloxy or alkyl- or dialkyl-amino, wherein the alkyl radicals contain 1–4 carbon atoms, or by indolyl or phenyl, which is unsubstituted or substituted by 1, 2 or 3 substituents from the group comprising halogen, nitro, C$_1$–C$_4$-alkyl or C$_1$–C$_4$-alkoxy, it also being possible for the substituents to differ independently of one another in the case of polysubstitutions, or R$^1$ is saturated C$_5$–C$_7$-cycloalkyl, which is optionally benzo-fused, or R$^1$ is aryl or heteroaryl, which is unsubstituted or in turn substituted by 1, 2 or 3 substituents from the group comprising halogen, nitro, cyano, C$_1$–C$_4$-alkyl and C$_1$–C$_4$-alkoxy, it also being possible for the substituents to differ independently of one another in the case of polysubstitutions, or R$^1$, provided that R$^2$ is H, is amino, which is unsubstituted or mono- or disubstituted by C$_1$–C$_4$-alkyl, phenyl or C$_1$–C$_3$-alkylcarbonyl, and R$^2$ is hydrogen or R$^1$, R$^2$ and R$^1$ being identical or different, or in which the radicals R$^1$ and R$^2$, together with the nitrogen atom, form a radical of the formula

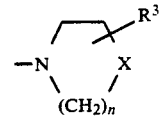

in which
n is 1 to 3 and
x is O, S, CH$_2$ or N-R$^3$,
in which
R$^3$ is hydrogen, phenyl or C$_1$–C$_6$-alkyl, C$_2$–C$_6$-alkenyl or C$_2$–C$_6$-alkynyl, these phenyl, alkyl, alkenyl and alkynyl- radicals being unsubstituted or mono- or polysubstituted by:
phenyl, which is in turn unsubstituted or mono- or polysubstituted by one or more substituents chosen from: halogen, nitro, cyano, carboxyl, hydroxyl, methyl, ethyl, methoxy, ethoxy and trifluoromethyl, or
N(R$^4$)$_2$, in which R$^4$ is H or C$_1$–C$_3$-alkyl, or
CON(R$^6$)$_2$ or CONHR$^6$, in which R$^6$ is H or C$_1$–C$_3$-alkyl, or
CON(R$^6$)$_2$ or CONHR$^6$, in which R$^6$ is H or C$_1$–C$_3$-alkyl, or in which (R$^6$)$_2$ represents a C$_1$–C$_6$-alkylene chain in which no CH$_2$ group or a CH$_2$ group which is not directly adjacent to the nitrogen atom is replaced by O, S or N-R$^4$,
or in which R$^3$ is C$_1$–C$_4$-alkoxy-carbonyl or C$_3$–C$_7$-cycloalkyl, and the physiologically tolerated salts, likewise effectively inhibit lysine hydroxylase and proline hydroxylase in the animal model.

This result is particularly surprising because the pharmacological activity of pyridines and pyridine derivatives evidently cannot also be transferred easily to the corresponding pyrimidines and pyrimidine derivatives. Thus, for example, the corresponding lipid-lowering pyrimidine analog of nicotinic acid is unknown. The same applies to the pyrimidine analog of isoniazide, which is employed as a tuberculosis agent.

The invention particularly relates to pyrimidine-4,6-dicarboxylic acid diamides according to formula I, in which $R^1$ is $C_1-C_{12}$-alkyl, which is unsubstituted or mono- or, in the case of $C_2-C_{12}$-alkyls, also polysubstituted by phenyl, hydroxyl, alkoxy, amino, alkoxycarbonyl or alkyl- or dialkylamino, in which the alkyl radicals contain 1-3 carbon atoms, or $\pi R^1$ is phenyl, which is unsubstituted or in turn monosubstituted by halogen, nitro, cyano, methyl or methoxy, or $R^1$, provided that $R^2$ is H, is amino, which is unsubstituted or monosubstituted by $C_1-C_3$-alkyl, phenyl or $C_1-C_3$-alkylcarbonyl, and $R^2$ is hydrogen, or in which the radicals $R^1$ and $R^2$, together with the nitrogen atom, form a radical of the formula

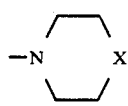

in which

X is O, $CH_2$ or $N-R^3$, in which $R^3$ is hydrogen or $C_1-C_3$-alkyl, and the physiologically tolerated salts.

By halogen there are understood fluorine, chlorine, bromine and iodine, by aryl there are understood phenyl and naphthyl and by heteroaryl there are understood 5-and 6-membered aromatic rings having 1, 2 or 3 nitrogen and/or oxygen and/or sulfur atoms, which can optionally also be benzo-fused; the heteroaryl radicals are, in particular, pyridyl, pyridazyl, pyrimidyl, pyrazyl, 1,3,5-triazyl, pyrolyl, pyrazolyl, imidazolyl, triazolyl, thienyl, oxazolyl and thiazolyl radicals and if appropriate benzo-fused compounds thereof.

"Polysubstituted" above and below means that at least 2 and at most all of the hydrogen atoms present in the alkyl, alkenyl, alkynyl, heteroaryl and aryl radicals are replaced by the substituents mentioned. In the case of polysubstitution, the substituents can also differ independently of one another.

All the alkyl and alkenyl radicals mentioned having more than 2 carbon atoms and all the alkynel radicals having more than 3 carbon atoms can be either straight-chain or branched.

The invention furthermore relates to the compounds of the formula I for use as pharmaceuticals. The invention moreover relates to the compounds of the formula I and pyrimidine-4,6-dicarboxylic acid diamide ($R^1=R^2=H$) for use as fibrosuppressants and immunosuppressants, as well as for inhibition of proline hydroxylase and lysine hydroxylase and for influencing the metabolism of collagen and collagen-like substances or the biosynthesis of Clq.

The invention furthermore relates to a process for the preparation of compounds of the formula I, which comprises reacting a compound of the formula II

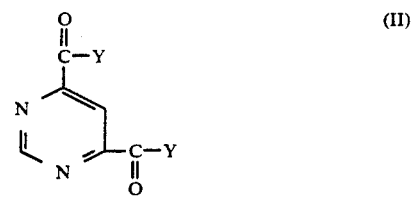

with a compound of the formula III, IV or V

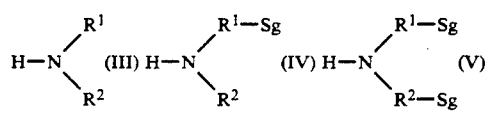

in which $R^1$ and $R^2$ have the meanings given in the case of formula I and Y is halogen, hydroxyl or $C_1-C_4$-alkoxy or, together with the carbonyl group, forms an active ester or a mixed anhydride, and Sg is a protective group, and subsequently removing any protective group present in the compound of the formula I, and if appropriate converting the reaction products into their physiologically tolerated salts.

The preparation of compounds according to formula I and the preparation of the starting substances required for this—where they are not commercially available—are described in more detail below.

The compounds according to the invention are prepared most simply by bringing together the two components, the pyrimidine derivative according to formula (II) and the amine according to formula (III), (IV) or (V) in equimolar amounts or with up to an approximately 5-fold excess of III, IV or V, and reacting them at temperatures between $-30°$ and $150°$ C., preferably at $20°$ to $100°$ C., until the reaction has ended. The end of the reaction can be determined, for example, by means of thin layer chromatography. One variant of this process comprises using a suitable solvent, such as diethyl ether, dimethoxyethane or tetrahydrofuran, chlorinated hydrocarbons, such as methylene chloride, chloroform or tri- or tetrachloro-ethylene, benzene, toluene or polar solvents, such as dimethylformamide, acetone, alcohols, such as methanol or ethanol, or dimethyl sulfoxide. An excess of amine according to formula (III), (IV) or (V), which can be up to approximately 5 times the amount, can also be used here. The reaction temperatures in this reaction are between room temperature and the boiling point of the solvent, temperatures in the range from room temperature to $130°$ C. being particularly preferred.

The reaction can likewise be carried out via a fixed anhydride, such as ethyl chloroformate, or via an activated ester, such as the paranitrophenyl ester ($Y=ClCh_2-COO$ or $NO_2-C_6H_4-O$). Corresponding methods are described in the literature.

If appropriate, the reaction can also be carried out in the presence of bases. Examples of additional bases are carbonates or bicarbonates, such as sodium carbonate, potassium carbonate, sodium bicarbonate or potassium bicarbonate, or tertiary amines, such as triethylamine, tributylamine, ethyldiisopropylamine or heterocyclic amines, such as N-alkylmorpholine, pyridine, quinoline or dialaylanilines.

If the reaction of compounds of the formula II is carried out with amines of the formula IV or V, the protective group Sg is subsequently stripped off under the conditions which are suitable for the protective group chosen and are described in the literature. Those compounds of the formula I which contain, for example, free OH, $NH_2$ or COOH groups in the substituents $R^1$ and/or $R^2$ can be prepared in this manner. Thus, for example, to prepare the N,N'-bis(hydroxyalkyl)-pyrimidine-4,6-dicarboxylic acid diamides, a procedure is preferably followed in which a corresponding bis(alkoxyalkyl)diamide, preferably bis(methoxyalkyl)diamide, is converted into the corresponding bis(hydroxyalkyl)diamide by processes which are known from the literature, for example with boron tribromide.

If appropriate, the products can be worked up, for example, by extraction or by chromatography, for example over silica gel. The product isolated can be recrystallized and if appropriate reacted with a suitable acid to give a physiologically tolerated salt. Examples of possible suitable acids are: mineral acids, such as hydrochloric and hydrobromic acid, as well as sulfuric, phosphoric, nitric or perchloric acid, or organic acids, such as formic, acetic, propionic, succinic, glycolic, lactic, malic, tartaric, citric, maleic, fumaric, phenylacetic, benzoic, methane-sulfonic, toluenesulfonic, oxalic, 4-aminobenzoic, naphthalene-1,5-disulfonic or ascorbic acid.

The starting compounds of the formula (III), where they are not commercially available, can be synthesized in a simple manner (for example Organikum, Organisch Chemisches Grundpraktikum (Basic Practical Organic Chemistry), 15th edition, VEB Deutscher Verlag der Wissenschaften, 1976; a review of the various possibilities is to be found in the Method Register, page 822). The amines of the formulae IV and V are obtained, where they are not commercially available, by processes which are known from the literature from the unprotected compounds by reaction with a protective group Sg (amino- and carboxy-protective groups: Houben-Weyl, Methoden der organischen Chemie (Methods of Organic Chemistry), Volume E5, pages 496-504, 1985; hydroxy-protective groups: Houben-Weyl, Methoden der organischen Chemie (Methods of Organic Chemistry), Volume VI/1b Alkohole (Alcohols) III, pages 735-783, 4th edition, Georg Thieme Verlag Stuttgart, N.Y. 1984). Examples of suitable amino-protective groups are Pyoc, Fmoc, Tcboc, Z, Boc, Ddz, Dobz or Moc. Examples of suitable carboxy- and/or hydroxy-protective groups are OMe, OBzl, ONbzl, OMbzl, OPic Bu' or Pac.

The starting compounds of the formula (II) are obtained, for example, by converting pyrimidine-4,6-dicarboxylic acid into the corresponding pyrimidine-4,6-dicarboxylic acid halide, preferably chloride (by processes which are known from the literature), preferably in the presence of a catalyst, such as dimethylformamide. This acid halide can then be reacted, for example, either with a suitable alcohol, for example paranitrobenzyl alcohol, to give the corresponding active ester, or with lower alcohols, such as methanol or ethanol, to give the corresponding esters. The pyrimidine-4,6-dicarboxylic acid can likewise also first be converted into a mixed anhydride by addition of a suitable carboxylic acid or a carboxylic acid ester, such as ethyl chloroformate, the mixed anhydride then being reacted with the amines (III), (IV) or (V) to give the products according to the invention. A corresponding method is likewise described in the literature.

The pyrimidine-4,6-dicarboxylic acid is prepared by processes which are known from the literature, for example by oxidation of 4,6-dimethylpyrimidine, which is in turn obtainable, for example, by catalytic hydrogenation of commercially available 2-mercapto-4,6-dimethyl-pyrimidine.

The compounds of the formula I according to the invention have valuable pharmacological properties and in particular exhibit an activity as inhibitors of proline hydroxylase and lysine hydroxyl-ase, and as a fibrosuppressant and immunosuppressant.

On the basis of these pharmacological properties, the compounds according to the invention are suitable for the treatment of disturbances in the metabolism of collagen and collagen-like substances, and for the treatment of disturbances of the biosynthesis of Clq.

The invention therefore also relates to the use of the compounds of the formula I according to the invention and physiologically tolerated salts thereof in the treatment of the abovementioned metabolic disturbances.

The compounds can be used as pharmaceuticals either by themselves or as a mixture with physiologically tolerated auxiliaries or excipients. For this purpose, they can be administered orally in doses of 0.01-25.0 mg/kg/day, preferably 0.01-5.0 mg/kg/day, or parenterally in doses of 0.001-5 mg/kg/day, preferably 0.001-2.5 mg/kg/day, in particular 0.005-1.0 mg/kg/day. In severe cases, the dosage can also be increased. However, lower doses are also sufficient in many cases. These data relate to an adult weighing about 75 kg.

The invention furthermore relates to the use of the compounds according to the invention in the preparation of pharmaceuticals which are employed for the treatment and prophylaxis of the abovementioned metabolic disturbances.

The invention also relates to pharmaceuticals which contain one or more of the compounds of the formula I according to the invention and/or physiologically tolerated salts thereof.

The pharmaceuticals are prepared by processes which are known per se and with which the expert is familiar. The pharmacologically active compounds (be active compound) according to the invention are employed as pharmaceuticals either as such or, preferably, in the form of tablets, coated tablets, capsules, suppositories, emulsions, suspensions or solutions in combination with suitable pharmaceutical auxiliaries or excipients, the active compound content being up to about 95%, advantageously between 10 and 75%.

Examples of suitable auxiliaries and excipients for the desired pharmaceutical formulation are, in addition to solvents, gel-forming agents, suppository bases, tablet auxiliaries and other active compound carriers, also for example antioxidants, dispersing agents, emulsifiers, foam suppressants, flavor correctants, preservatives, solubilizing agents or dyestuffs.

The active compounds can be administered orally, parenterally or rectally.

The active compounds are mixed with the additives suitable for this purpose, such as excipients, stabilizers or inert diluents, and brought into suitable administration forms, such as tablets, coated tablets, hard gelatine capsules, aqueous alcoholic or oily suspensions or aqueous or oily solutions, by the customary methods. Inert excipients which can be used are, for example, gum arabic, magnesia, magnesium carbonate, potassium phosphate, lactose, glucose or starch, in particular maize starch. The formulation can be carried out here either on dry or on moist granules. Examples of possible oily excipients or solvents are vegetable or animal oils, such as sunflower oil or cod-liver oil.

For subcutaneous or intravenous administration, if desired the active compounds are dissolved, suspended or emulsified using substances suitable for this, such as solubilizing agents, emulsifiers or other auxiliaries. Possible solvents are, for example, physiological saline solution or alcohols, for example ethanol, propanol or glycerol, and in addition also sugar solutions, such as solutions of glucose or mannitol, or a mixture of the various solvents mentioned.

The invention is explained in more detail below with the aid of examples.

Example 1

Pyrimidine 4,6-dicarboxylic acid di-(2-methoxyethyl)-amide (formula I: $R^1 = CH_2\text{-}CH_2\text{-}OCH_3$; $R^2 = H$)

1.7 g of pyrimidine-4,6-dicarboxylic acid are suspended in 20 ml of toluene, and 2.4 g of thionyl chloride and 0.2 ml of dimethylformamide are added. The mixture is heated to the reflux temperature until no further evolution of gas is to be observed (about 3 hours). About 5 ml of solvent are distilled off, the mixture is cooled to 0°–10° C. and 1.9 g of 2-methoxyethylamine and 2.8 ml of triethylamine, dissolved in 10 ml of toluene, are added. The solution is heated slowly to room temperature, stirred at room temperature for 12 hours and evaporated to dryness. The residue is taken up in 50 ml of methylene chloride, the mixture is extracted 3 times by shaking with saturated sodium bicarbonate solution and the organic phase is washed with water, dried with magnesium sulfate and evaporated.

The solid is recrystallized from diisopropyl ether. Yield: 2.1 g; melting point: 85°–86° C.

Example 2

Pyrimidine-4,6-dicarboxylic acid dibenzylamide (formula I: $R^1 = CH_2-$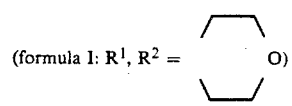; $R^2 = H$)

For the course of the experiment, see Example 1:
Mixture:
1.7 g of pyrimidine-4,6-dicarboxylic acid
2.7 g of benzylamine
Yield: 2.1 g; melting point: 131°–132° C. (from diisopropyl ether)

Example 3

Pyrimidine-4,6-dicarboxylic acid diethylamide (formula I: $R^1 = CH_2\text{-}CH_3$; $R^2 = H$)

For the course of the experiment, see Example 1
Mixture:
1.7 g of pyrimidine-4,6-dicarboxylic acid
1.6 g of ethylamine hydrochloride
Yield: 1.1 g; melting point: 185°–186° C. (from petroleum ether)

Example 4

4,6-Di-[(morpholin-1-yl)-carbonyl]-pyrimidine (formula I: $R^1, R^2 =$ 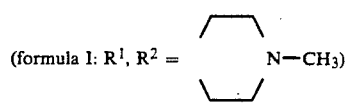)

For the course of the experiment, see Example 1
Mixture:
1.7 g of pyrimidine-4,6-dicarboxylic acid
2.2 g of morpholine
Yield: 2.4 g; melting point: 175° C. (from diisopropyl ether)

Example 5

Pyrimidine-4,6-dicarboxylic acid di-(3-methoxy-propyl)-amide (formula I: $R^1 = (CH_2)_3\text{-}OCH_3$; $R^2 = H$)

For the course of the experiment, see Example 1:
Mixture:
8.4 g of 4,6-pyrimidine-dicarboxylic acid
11.2 g of 3-methoxypropylamine
Yield: 8.5 g; melting point: 64° C. (from diisopropyl ether)

Example 6

Pyrimidine-4,6-dicarboxylic acid di-dodecylamide (formula I: $R^1 = (CH_2)_{11}\text{-}CH_3$; $R^2 = H$)

For the course of the experiment, see Example 1:
Mixture:
0.8 g of pyrimidine-4,6-dicarboxylic acid
2.4 g of dodecylamine
Yield: 2.2 g; melting point: 78°–79° C. (from diisopropyl ether)

Example 7

4,6-Di-[(1-methylpiperazin-4-yl)-c-arbonyl]-pyrimidine (formula I: $R^1, R^2 =$ ⟨N-CH$_3$⟩)

For the course of the experiment, see Example 1:
Mixture:
0.8 g of pyrimidine-4,6-dicarboxylic acid
1.3 g of 1-methylpiperazine
Yield: 1.1 g; melting point: 162° C. (from petroleum ether)

Example 8

Pyrimidine-4,6-dicarboxylic acid di-(2-diethylamino-ethyl)-amide (formula I: $R^1 = -(CH_2)_2\text{-}N(C_2H_5)_2$; $R^2 = H$)

For the course of the experiment, see Example 1:
Mixture:
0.8 g of pyrimidine-4,6-dicarboxylic acid
1.5 g of 2-diethylamine-ethylamine
Yield: 0.9 g; melting point: 72° C. (from petroleum ether)

Example 9

Pyrimidine-4,6-dicarboxylic acid di-(2,2-dimethoxy-ethyl)-amide (formula I: $R^1 = CH_2\text{-}CH(OCH_3)_2$; $R^2 = H$)

For the course of the experiment, see Example 1:
Mixture:
0.8 g of pyrimidine-4,6-dicarboxylic acid
1.3 g of aminoacetaldehyde dimethyl acetal
Yield: 1.0 g; melting point: 107° C. (from petroleum ether)

Example 10

Pyrimidine-4,6-dicarboxylic acid di-anilide

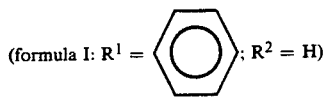

(formula I: $R^1 = $ phenyl; $R^2 = H$)

For the course of the experiment, see Example 1:
Mixture:
0.8 g of pyrimidine4,6-dicarboxylic acid
1.2 g of aniline
Yield: 0.8 g; melting point: 225° C. (from petroleum ether)

Example 11

Pyrimidine-4,6-dicarboxylic acid di-(2-methoxy-iso-propyl)-amide (formula I: $R^1 = CH(CH_2OCH_3)CH_3$; $R^2 = H$)

For the course of the experiment, see Example 1:
Mixture:
0.8 g of pyrimidine-4,6-dicarboxylic acid
1.1 g of 2-amino1-methoxy-propane
Yield: 1.0 g; melting point: 55° C. (from petroleum ether)

Example 12

Pyrimidine-4,6-dicarboxylic acid di-(2-hydroxy-ethyl)-de (formula I: $R^1 = CH_2\text{—}CH_2\text{—}OH$; $R^2 = H$)

0.9 g of pyrimidine-4,6-dicarboxylic acid di-(2-methoxy-ethyl)-amide from Example 1 is dissolved in 5 ml of methylene chloride at room temperature, the solution is cooled to $-78°$ C. and 18 ml of boron tribromide (1M solution in methylene chloride) is slowly added dropwise over the course of 1 hour. The mixture is allowed to come to room temperature and is subsequently stirred for 3 hours. It is then poured onto 120 ml of sodium bicarbonate solution and extracted 3 times with ethyl acetate. The combined organic solutions are dried with magnesium sulfate and evaporated. The crude product is chromato-graphed on silica gel.
Yield: 0.8 g; melting point: 62° C.

Example 13

Pyrimidine-4,6-dicarboxylic acid di-(3-hydroxypropyl)-amide (formula I: $R^1 = (CH_2)_3\text{—}OH$; $R^2 = H$)

The compound is prepared analogously to Example 12 from pyrimidine-4,6-dicarboxylic acid di-(3-methoxypropy--1)-amide (Example 5).

Example 14

Pyrimidine-4,6-dicarboxylic acid dihydrazide (formula I: $R^1 = \text{—}NH_2$; $R^2 = H$)

2 g of dimethyl pyrimidine-4,6-dicarboxylate (prepared in accordance with the method of H. Yamada, Heterocycles, 13, 235 (1979)) are dissolved in 75 ml of methanol at room temperature. 1.1 g of hydrazine hydrate are added. A yellow precipitate is formed and is stirred for 3 hours and then filtered off with suction.
Yield: 1.9 g; melting point:

Example 15

Pyrimidine-4,6-dicarboxylic acid di-acetohydrazide (formula I: $R^1 = NH\text{-}C(O)\text{-}CH_3$; $R^2 = H$)

0.4 g of pyrimidine-4,6-dicarboxylic acid dihydrazide from Example 14 is suspended in 25 ml of methylene chloride at room temperature. 0.2 g of 4-dimethylamino-pyridine and 0.4 g of acetic anhydride are added and the mixture is stirred at room temperature for 12 hours. It is concentrated to dryness, the residue is extracted by stirring with ethyl acetate:cyclohexane 4:1 and the resulting residue is filtered off with suction and dried.
Yield: 0.33 g; melting point:

Example 16

Pharmacological activity

To demonstrate the effective inhibition of proline hydroxylase and lysine hydroxylase by the compounds according to the invention, the hydroxyproline concentrations in the liver and the procollagen III peptide and bilirubin concentrations in the serum of
a) untreated rats (control)
b) rats to which carbon tetrachloride had been administered ($CCl_4$ control)
c) rats to which first $CCl_4$ and then a compound according to the invention had been administered were measured (this test method is described by C. Rouiller, Experimental toxic injury of the liver; in The Liver, C. Rouiller, volume 2, pages 335–476, New York, Academic Press, 1964).

The action potency of the compounds according to the invention was determined as the percentage inhibition of the liver hydroxyproline and procollagen III peptide and bilirubin synthesis following oral administration in comparison with control animals to which only carbon tetrachloride was administered ($CCl_4$ control). The results are shown in Table 1.

TABLE 1

| Action of prolyl-hydroxylase inhibitors on $CCl_4$— induced liver fibrosis in rats, 8-week treatment | | | | | |
|---|---|---|---|---|---|
| Compound | Dose mg/kg | N | Bilirubin[b] μM | PIIIP[c] ng/ml | Hyp[d] μg/ml |
| Control | | 20 | 1.9 | 11 | 0.056 |
| $CCl_4$ | | 56 | 4.5 | 32 | 0.228 |
| Increase[e] | | 36 | 2.6 | 21 | 0.172 |
| Example 3 | 50 | 17 | 2.8 | 26 | 0.200 |
| Increase[e] | | | 0.9 | 15 | 0.144 |
| Decrease[f] | | | 65 | 28 | 16% |
| Mean value[g] | | | (36 ± 15%) | | |
| Example 2 | 50 | 16 | 2.8 | 26 | 0.192 |
| Increase[e] | | | 0.9 | 28 | 0.136 |
| Decrease[f] | | | 65 | 28 | 21% |

TABLE 1-continued

Action of prolyl-hydroxylase inhibitors on CCl4—induced liver fibrosis in rats, 8-week treatment

| Compound | Dose mg/kg | N | Bilirubin[b] μM | PIIIP[c] ng/ml | Hyp[d] μg/ml |
|---|---|---|---|---|---|
| Mean value[g] | | | (38 ± 14%) | | |

[a] daily oral dose
[b] bilirubin in the serum (total)
[c] procollagen III N-peptide in the serum
[d] hydroxyproline content in the liver
[e] increase (absolute) in comparison with the control
[f] percentage decrease in the comparison with CCl4 treatment
[g] total content of bilirubin, PIIIP and Hyp, % deviation

We claim:

1. A pyrimidine-4,6-dicarboxylic acid diamide of the formula I

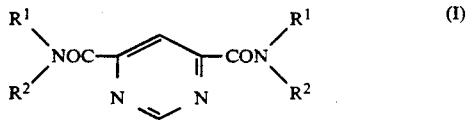

in which

R$^1$ is C$_1$–C$_{12}$alkyl, C$_2$–C$_{12}$-alkenyl or C$_2$–C$_{12}$-alkynyl, which are unsubstituted or monosubstituted or, in the case of C$_2$–C$_{12}$-alkyls, C$_2$–C$_{12}$-alkenyls and C$_2$–C$_{12}$-alkynyls, also polysubstituted by halogen, hydroxyl, cyano, amino, carboxyl, alkoxy, alkoxycarbonyl, alkylcarbonyloxy or alkyl- or dialkylamino, wherein the alkyl radicals contain 1-4 carbon atoms, or by indolyl or phenyl, which is unsubstituted or substituted by 1, 2 or 3 substituents from the group comprising halogen, nitro, C$_1$–C$_4$-alkyl or C$_1$–C$_4$ alkoxy, it also being possible for the substitutents to differ independently of one another in he case of polysubstitutions, or R$^1$ is saturated C$_5$–C$_7$-cycloalkyl, which is optionally benzo-fused, or R$^1$ is selected from phenyl, naphthyl, pyridyl, pyridazinyl, pyrimidinyl, pyrazinyl, 1,3,5-triazinyl, pyrrolyl, pyrazolyl, imidazolyl, triazolyl, thienyl, oxazolyl and thiazolyl, which R$^1$ is unsubstituted or in turn substituted by 1, 2 or 3 substitutents from the group consisting of halogen, nitro, cyano, C$_1$–C$_4$-alkyl and C$_1$–C$_4$ -alkoxy, it also being possible for the substitutents to differ independently of one another in the case of polysubstitutions, or R$^1$, provided that R$^2$ is H, is amino, which is unsubstituted or mono- or disubstituted by C$_1$–C$_4$-alkyl, phenyl or C$_1$–C$_3$-alkylcarbonyl, and R$^2$ is hydrogen or R$^1$, R$^2$ and R$^1$ being identical or different, or in which the radicals R$^1$ and R$^2$, together with the nitrogen atom, form a radical of the formula

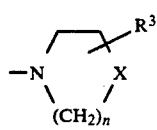

in which n is 1 to 3 and x is O, S, CH$_2$ or N-R$^3$, in which R$^3$ is hydrogen, phenyl or C$_1$–C$_6$-alkyl, C$_2$–C$_6$-alkenyl or C$_2$–C$_6$-alkynyl, these phenyl, alkyl, alkenyl and alkynyl radicals being unsubstituted or mono- or polysubstituted by:

a) phenyl, which is in turn unsubstituted or mono- or polysubstituted by one or more substitutents chosen from: halogen, nitro, cyano, carboxyl, hydroxyl, methyl, ethyl, methoxy, ethoxy and trifluoromethyl, or b) N(R$^4$)$_2$, in which R$^4$ is H or C$_1$–C$_3$-alkyl, or c) COOR$^5$, in which R$^5$ is H or C$_1$–C$_3$-alkyl, or d) CON(R$^6$)$_2$ or COHNHR$^6$, in which R$^6$ is H or C$_1$–C$_3$-alkyl, or in which (R$^6$)$_2$ represents a C$_4$–C$_6$-alkylene chain in which no CH$_2$ group is replaced by O, S or N-R$^4$, or in which R$^3$ is C$_1$–C$_4$-alkoxy-carbonyl or C$_3$–C$_7$-cycloalkyl, or a physiologically tolerated salt.

2. A pyrimidine-4,6-dicarboxylic acid diamide of the formula I as claimed in claim 1, in which R$^1$ is C$_1$–C$_{12}$-alkyl, which is unsubstituted or mono- or, in the case of C$_2$–C$_{12}$-alkyls, also polysubstituted by phenyl, hydroxyl, aloxy, amino, alkoxycarbonyl or alkyl- or dialkylamino, in which the alkyl radicals contain 1-3 carbon atoms, or R$^1$ is phenyl, which is unsubstituted or in turn monosubstituted by halogen, nitro, cyano, methyl or methoxy, or R$^1$, provided that R$^2$ is H, is amino, which is unsubstituted or monosubstituted by C$_1$–C$_3$-alkyl, phenyl or C$_1$–C$_3$-alkylcarbonyl, and R$^2$ is hydrogen, or in which the radicals R$^1$ and R$^2$, together with the nitrogen atom, form a radical of the formula

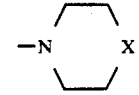

in which

X is O, CH$_2$ or N-R$^3$, in which

R$^3$ is hydrogen or C$_1$–C$_3$-alkyl, or a physiologically tolerated salt.

3. A pyrimidine-4,6-dicarboxylic acid diamide of the formula I as claimed in claim 1, in which R$^1$ is C$_1$–C$_{12}$-alkyl, which is unsubstituted or mono- or, in the case of C$_2$–C$_{12}$-alkyls, also polysubstituted by phenyl, hydroxyl, alkoxy, alkoxycarbonyl or dialkyl-amino, in which the alkyl radicals contain 1-3 carbon atoms, or R$^1$ is phenyl, or R$^1$, provided that R$^2$ is H, is amino, which is unsubstituted or monosubstituted by methylcarbonyl, and R$^2$ is hydrogen, or in which the radicals R$^1$ and R$^2$, together with the nitrogen atom, form a radical of the formula

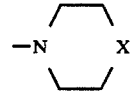

in which

X is O, CH$_2$ or N-R$^3$, in which

R$^3$ is hydrogen or methyl, or a physiologically tolerated salt.

4. A pharmaceutical composition comprising an effective amount of the diamide of claim 1 and a pharmaceutically acceptable carrier.

5. A pharmaceutical composition for inhibition of proline hydroxylase or lysine hydroxylase comprising an effective amount of the diamide of claim 1 and of pyrimidine-4,6-dicarboxylic acid diamide and a pharmaceutically acceptable carrier.

6. A fibrosuppressant or immunosuppressant composition comprising an effective amount of the diamide of claim 1 and of pyrimidine-4,6-dicarboxylic acid diamide and a pharmaceutically acceptable carrier.

7. A pharmaceutical composition for influencing the metabolism of collagen and collagen-like substances and the biosynthesis of $Cl_q$ comprising an effective amount of the diamide of claim 1 and of pyrimidine-4,6-dicarboxylic acid diamide and a pharmaceutically acceptable carrier.

8. A method for treatment of disturbances in the metabolism of collagen and collagen-like substances or the biosynthesis of $Cl_q$ comprising treating a living organism affected by said disturbances with an effective amount of the diamide of claim 1 and of pyrimidine-4,6-dicarboxylic acid diamide in a pharmaceutically acceptable carrier.

* * * * *

UNITED STATES PATENT AND TRADEMARK OFFICE
CERTIFICATE OF CORRECTION

PATENT NO. : 5,130,317

DATED : July 14, 1992

INVENTOR(S) : Ekkehard Baader et al.

It is certified that error appears in the above-identified patent and that said Letters Patent is hereby corrected as shown below:

Claim 1, Column 11, Line 25, change "$C_1-C_{12}$alkyl" to --$C_1-C_{12}$-alkyl--;

Claim 1, Column 11, Line 35, change "$C_1-C_4$alkoxy" to --$C_1-C_4$-alkoxy--;

Claim 1, Column 11, Line 36, change "substitutents" to --substituents--;

Claim 1, Column 11, Line 37, change "he" to --the--;

Claim 1, Column 11, Line 45, change "substitutents" to --substituents--;

Claim 1, Column 11, Line 48, change "substitutents" to --substituents--;

Claim 1, Column 11, Line 66, change "x" to --X--;

UNITED STATES PATENT AND TRADEMARK OFFICE
CERTIFICATE OF CORRECTION

| | | |
|---|---|---|
| PATENT NO. : | 5,130,317 | |
| DATED : | July 14, 1992 | |
| INVENTOR(S) : | Ekkehard Baader et al. | |

It is certified that error appears in the above-identified patent and that said Letters Patent is hereby corrected as shown below:

Claim 1, Column 12, Line 4, change "substitutents" to --substituents--; and

Claim 1, Column 12; Line 10, change "COHNHR$^6$" to --CONHR$^6$--.

Claim 2, Column 12, Line 20, change "aloxy" to --alkoxy--.

Signed and Sealed this

Fourth Day of January, 1994

Attest:

BRUCE LEHMAN

*Attesting Officer*    *Commissioner of Patents and Trademarks*